United States Patent
Nguyen et al.

(10) Patent No.: US 10,088,456 B2
(45) Date of Patent: Oct. 2, 2018

(54) SCANNING ACOUSTIC MICROSCOPY SYSTEM AND METHOD

(71) Applicant: Texas Instruments Incorporated, Dallas, TX (US)

(72) Inventors: Dat Tan Nguyen, Murphy, TX (US); Robert Milotta, Wylie, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 792 days.

(21) Appl. No.: 14/230,443

(22) Filed: Mar. 31, 2014

(65) Prior Publication Data
US 2015/0276681 A1    Oct. 1, 2015

(51) Int. Cl.
| | | |
|---|---|---|
| G01R 31/10 | (2006.01) | |
| G01N 29/28 | (2006.01) | |
| G01N 29/06 | (2006.01) | |
| G01N 29/44 | (2006.01) | |

(52) U.S. Cl.
CPC ......... *G01N 29/28* (2013.01); *G01N 29/0681* (2013.01); *G01N 29/4427* (2013.01); *G01N 2291/0231* (2013.01)

(58) Field of Classification Search
CPC ............... G01N 29/28; G01N 29/4427; G01N 29/0681; G01N 2291/0231
USPC .......... 324/750.09, 500, 537, 750.01, 750.03
See application file for complete search history.

(56) References Cited

U.S. PATENT DOCUMENTS

| | | | | |
|---|---|---|---|---|
| 5,423,479 A | * | 6/1995 | Nichols | G05D 23/1919 236/49.3 |
| 5,668,342 A | * | 9/1997 | Discher | F42B 33/06 102/293 |
| 5,814,731 A | * | 9/1998 | Alexander | G01N 29/225 73/624 |
| 9,910,053 B2 | * | 3/2018 | Bakhru | G01N 33/86 |
| 2002/0189359 A1 | * | 12/2002 | Batzinger | G01N 29/28 73/596 |
| 2003/0219060 A1 | * | 11/2003 | Sloneker | G01K 7/021 374/112 |
| 2004/0123968 A1 | * | 7/2004 | Osanai | B22D 19/00 164/98 |
| 2006/0016469 A1 | * | 1/2006 | Kondoh | H01L 35/28 136/201 |
| 2008/0022774 A1 | * | 1/2008 | Lu | G01N 29/0681 73/606 |
| 2008/0257050 A1 | * | 10/2008 | Watanabe | G01S 7/521 73/627 |
| 2014/0320144 A1 | * | 10/2014 | Nakaya | H01M 10/54 324/434 |
| 2017/0264110 A1 | * | 9/2017 | Toya | H02J 7/0021 |

* cited by examiner

*Primary Examiner* — Giovanni Astacio-Oquendo
(74) *Attorney, Agent, or Firm* — Ronald O. Neerings; Charles A. Brill; Frank D. Cimino

(57) ABSTRACT

A system for scanning and analyzing a device under test includes a transducer. The transducer transmits ultrasonic waves to scan the device under test and determine various properties (e.g., material of layers). The system further includes a heating/cooling portion. The heating/cooling portion conducts thermal stress testing on the device under test to accentuate areas of delamination between layers. The transducer then performs scans on the device under test to locate areas of delamination.

30 Claims, 8 Drawing Sheets

SCANNING ACOUSTIC MICROSCOPY SYSTEM AND METHOD

BACKGROUND

Conventionally, scanning acoustic microscopy (SAM) systems have been used to find delamination areas in chip packages. For example, a SAM system may scan a sampled batch of chips to determine whether any chips have areas of delamination between layers. An area of delamination is defined as a significant gap or separation between layers of a device under test (DUT). If delamination is discovered, then a chip or batch of chips may then be categorized as faulty and subsequently discarded.

Conventional SAM systems are used to determine imperfections/delaminations between layers of devices. These properties can subsequently be analyzed. A conventional SAM system will now be described in more detail in FIG. 1.

FIG. 1 illustrates a conventional SAM system 100.

As shown in the figure, conventional SAM system 100 includes an ultrasonic transducer 102, an acoustic conductive bath 104, a detector 106 and a DUT 108. DUT 108 includes an encapsulating shell 118, an inner layer 120 and a delamination 122. Encapsulating shell 118 has a top surface 124 and a bottom surface 126. Inner layer 120 has a top surface 128 and a bottom surface 130.

In SAM system 100, acoustic conductive bath 104 is filled with water and DUT 108 is submerged in acoustic conductive bath 104.

Ultrasonic transducer 102 is placed on the surface of acoustic conductive bath 104 and transmits ultrasonic waves to DUT 108. Some of these ultrasonic waves will penetrate an interface from one media to another and some of the ultrasonic waves will transmit into and through the interface. For example, some ultrasonic waves will reflect off of the various layers within DUT 108 and some ultrasonic waves will transmit through the various layers within DUT 108.

Detector 106 is placed beneath DUT 108 and is used to measure the information gathered from a transmissive ultrasonic wave 116. Similarly, ultrasonic transducer 102 measures the information gathered from reflective ultrasonic waves 111, 113 and 115.

As a result of this ultrasonic scanning process, through transmitting ultrasonic waves 110, 112 and 114 and receiving ultrasonic waves 113 and 115, the degree of separation between bottom surface 126 and top surface 128 can be determined. This degree of separation equates to various imperfections/delaminations between encapsulating shell 118 and inner layer 120. For example, delamination 122 is one such separation between the two adjacent layers.

In some cases, if the delaminations are smaller than the wavelength of the ultrasonic wave produced by the conventional SAM system scans, the delamination will not be detected. The frequencies of the ultrasonic waves may be increased in order to increase the resolution of a scan, thus detecting smaller delaminations. However, these frequency increases require much more power. Detecting small delaminations is important because if they are not detected, small delaminations may grow larger. This may not be detected until after the DUT is in use. The DUT may then fail.

Conventional SAM systems scan devices using transmissive and reflective ultrasonic waves, and then detect interfaces in the layers of a DUT using these ultrasonic waves. An example image from a conventional SAM system scan will now be described in more detail in FIG. 2.

FIG. 2 illustrates a planar view 200 from a conventional SAM system. As shown in the figure, planar view 200 includes a DUT 202. DUT 202 includes a delamination 204, a delamination 206 and a delamination 208.

As a result of the scan from the SAM system, delaminations 204, 206 and 208 are distinguishable from other areas in DUT 202. Therefore, DUT 202 is categorized as a faulty device. If it is determined that enough DUTs are faulty within a batch of manufactured devices, then the whole batch may be discarded. Alternatively, if it is determined that enough DUTs within a batch pass the scanning process and are not faulty, then the whole batch may be used.

Conventional SAM systems may detect some areas of delamination in a DUT. In some instances conventional SAM systems may not detect areas of delamination, but the DUT may fail when it is in use. This failure may be caused by undetected delaminations in the DUT, for example because the delaminations were smaller than the resolution of the SAM during the testing phase, but enlarged when the DUT was actually used What is needed is a system and method that increases the likelihood of detecting areas of delamination for a DUT and provides a way to determine other substantive properties of the device.

BRIEF SUMMARY

The present invention provides a system and method which uses thermal stress testing to increase the likelihood of detecting areas of delamination for a DUT and provides a way to determine other substantive properties of the device.

In accordance with aspects of the present invention, a method is provided wherein the method includes: submerging a DUT in an acoustic conductive bath, the DUT having a top layer and a second layer, the top layer being disposed between the second layer and the conductive bath, the top layer having a top surface in contact with the conductive bath; scanning, via an ultrasonic transducer, an area of the DUT; and obtaining, via a processing portion, a contour map of the top surface from the scanning.

Additional advantages and novel features of the invention are set forth in part in the description which follows, and in part will become apparent to those skilled in the art upon examination of the following or may be learned by practice of the invention. The advantages of the invention may be realized and attained by means of the instrumentalities and combinations particularly pointed out in the appended claims.

BRIEF SUMMARY OF THE DRAWINGS

The accompanying drawings, which are incorporated in and form a part of the specification, illustrate an exemplary embodiment of the present invention and, together with the description, serve to explain the principles of the invention. In the drawings.

DETAILED DESCRIPTION

Figure 1:
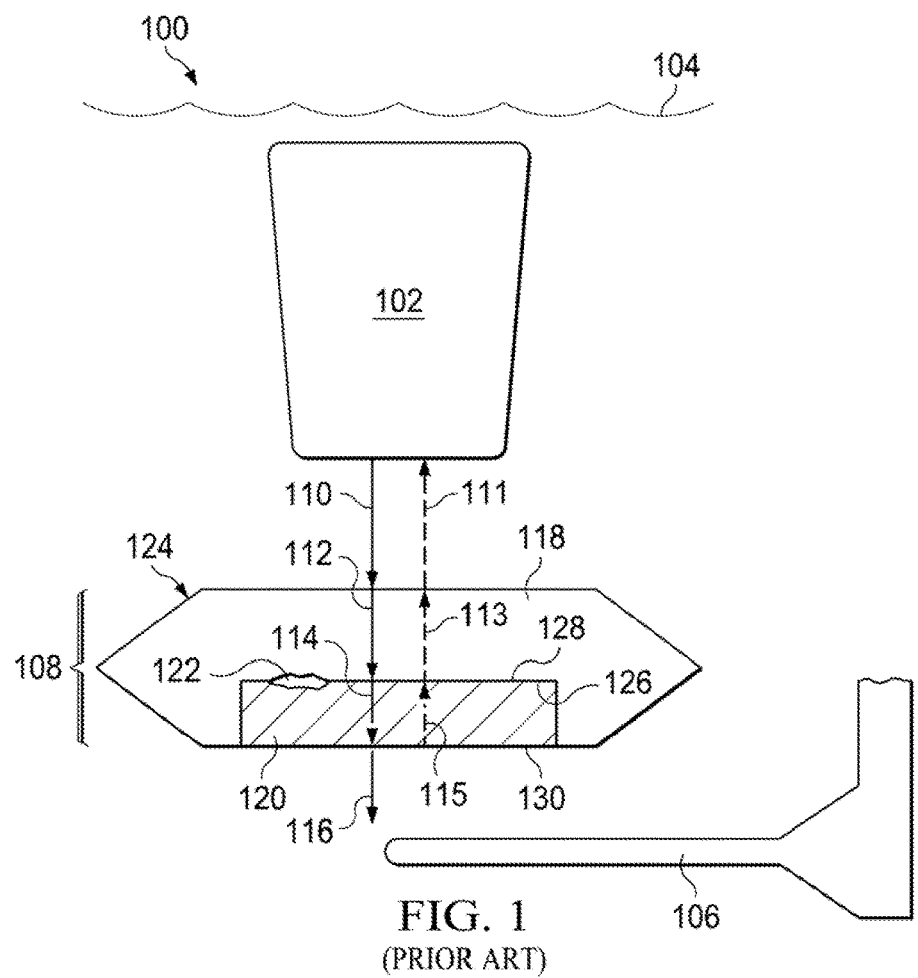
FIG. 1 illustrates an example conventional SAM system.
Figure 2:
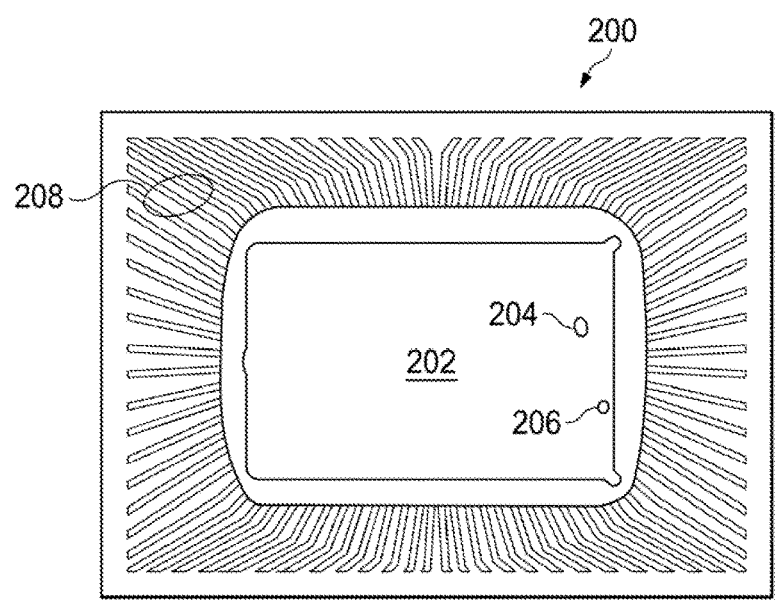
FIG. 2 illustrates a planar view of a scan of a DUT from a conventional SAM system.

In accordance with aspects of the present invention, a SAM system is used to scan a DUT that has been rotated ninety degrees so as to obtain a cross-sectional view showing the thicknesses of each layer of the DUT. Then, the SAM system is used to scan the DUT to obtain a planar contour map of the DUT by determining the time of travel of the reflected ultrasonic waves as reflected from each layer of the DUT. A time of travel through each material layer may be determined, as the thickness of each layer is known from the original scan.

Then, the velocity of the ultrasonic waves through each layer can be determined. A library associating velocities with known materials is used in conjunction with the recorded velocities in the DUT to identify the materials of each layer in the DUT. As such, the present invention enables a SAM system to identify the material of each layer in a DUT and identify the thickness of each layer in the DUT.

In accordance with other aspects of the present invention, delamination is accentuated for a DUT by subjecting the DUT to a thermal stress test. In particular, a DUT may be heated and/or cooled, such that as the DUT heats/cools, the different materials will expand/contract at different rates based on the coefficients of thermal expansion of each material of each layer, respectively. The different expansion or contraction rates of layers may accentuate the development of delamination between layers. In other words, if one layer were to expand at a greater rate than an adjacent layer, then the difference in the expansion rates may create a gap between the two layers.

The DUT is then scanned with the SAM system to determine if a delamination has occurred. If so, the device is considered faulty. This thermal stress test will identify DUTs that may not have delamination spots at one temperature, but would likely have developed delamination spots at a particular temperature in the environment in which the device would be operating. Therefore, by heating or cooling the DUT in accordance with aspects of the present invention, a particular operating temperature or particular environmental temperature at which the DUT would have been used can be emulated.

In accordance with another aspect of the present invention, the heating/cooling of the DUT is precisely controlled. In some embodiments, the temperature of the device heating/cooling the DUT is precisely controlled. In some embodiments, a heat sink is additionally used in combination with a heating/cooling device to maintain a precise temperature of the device heating/cooling the DUT. In some embodiments, the rate at which the heat sink can absorb heat from the DUT can be controlled. In some embodiments, the combination of controlling the heating/cooling device and the heat sink is used to control the temperature and the change in temperature of the heating/cooling device used to heat/cool the DUT.

Aspects of the present invention will be described in greater detail with reference to FIGS. 3-11.

A first aspect of determining the material layers of a DUT will now be described with reference to FIGS. 3-8E.

A method of using a SAM system to determine the material components and thicknesses of layers of a DUT in accordance with aspects of the present invention will be described in more detail with reference to FIG. 3.

Figure 3:
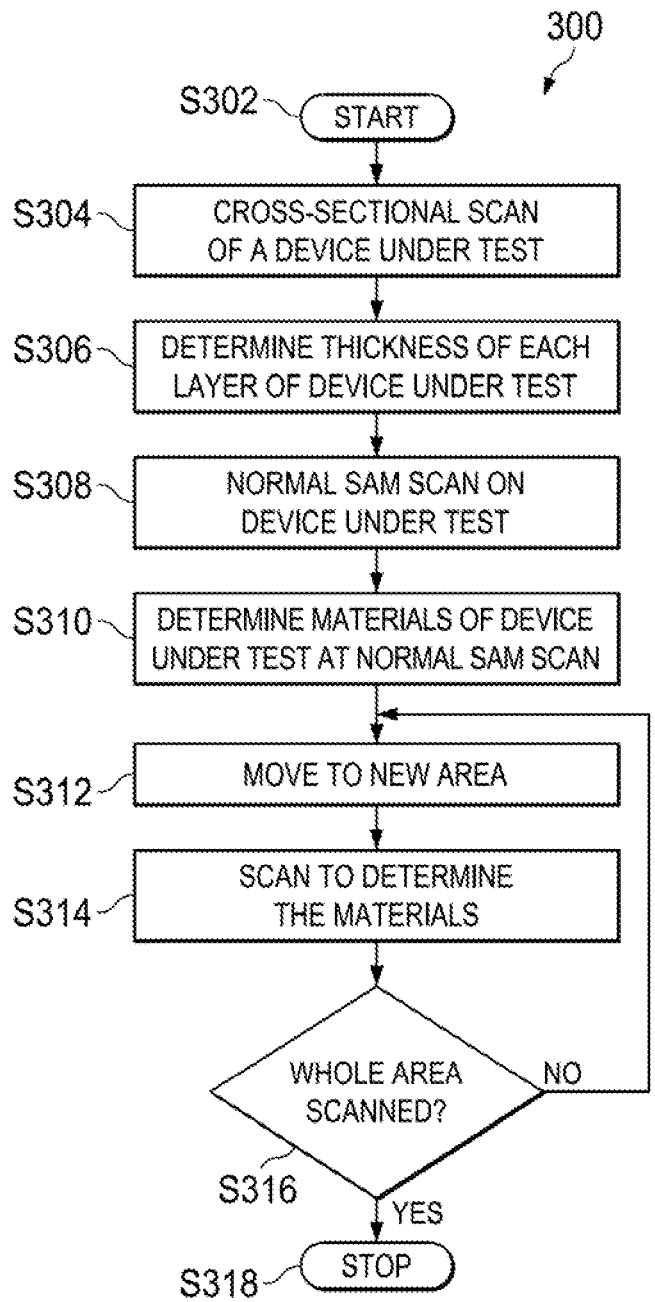
FIG. 3 illustrates an example method of scanning and determining various properties of a DUT, in accordance with aspects of the present invention.

FIG. 3 illustrates an example method 300 of determining the layers of a DUT using a SAM system, in accordance with aspects of the present invention.

Method 300 starts (S302) and a cross-sectional scan is performed on a DUT (S304). For example, with reference to FIG. 1, SAM system 100 may be used to scan DUT 108. However, in accordance with aspects of the present invention, DUT 108 would be rotated ninety degrees so that the cross-section of the device can be scanned. An example of a cross-section scan is illustrated in FIG. 4.

Figure 4:
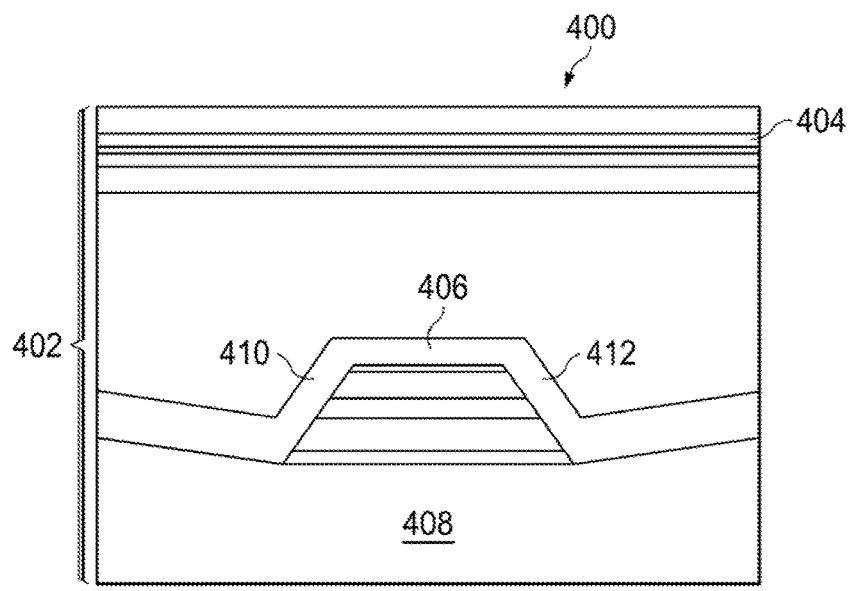
FIG. 4 illustrates a cross-sectional view of a DUT from a SAM system, in accordance with aspects of the present invention.

As shown in FIG. 4, cross-sectional view 400 includes a DUT 402. DUT 402 includes a top layer 404, a trapezoidal plateau 406 and a bottom layer 408. Trapezoidal plateau 406 includes a left side 410 and a right side 412. Cross-sectional view 400 clearly distinguishes each layer of DUT 402. The visual distinction between top layer 404 and bottom layer 408 is emphasized by trapezoidal plateau 406.

Returning to FIG. 3, the thickness of each layer of the DUT is then determined (S306). This may be accomplished with a SAM system in accordance with aspects of the present invention. For example, FIG. 5 illustrates a SAM system 500, in accordance with aspects of the present invention.

Figure 5:
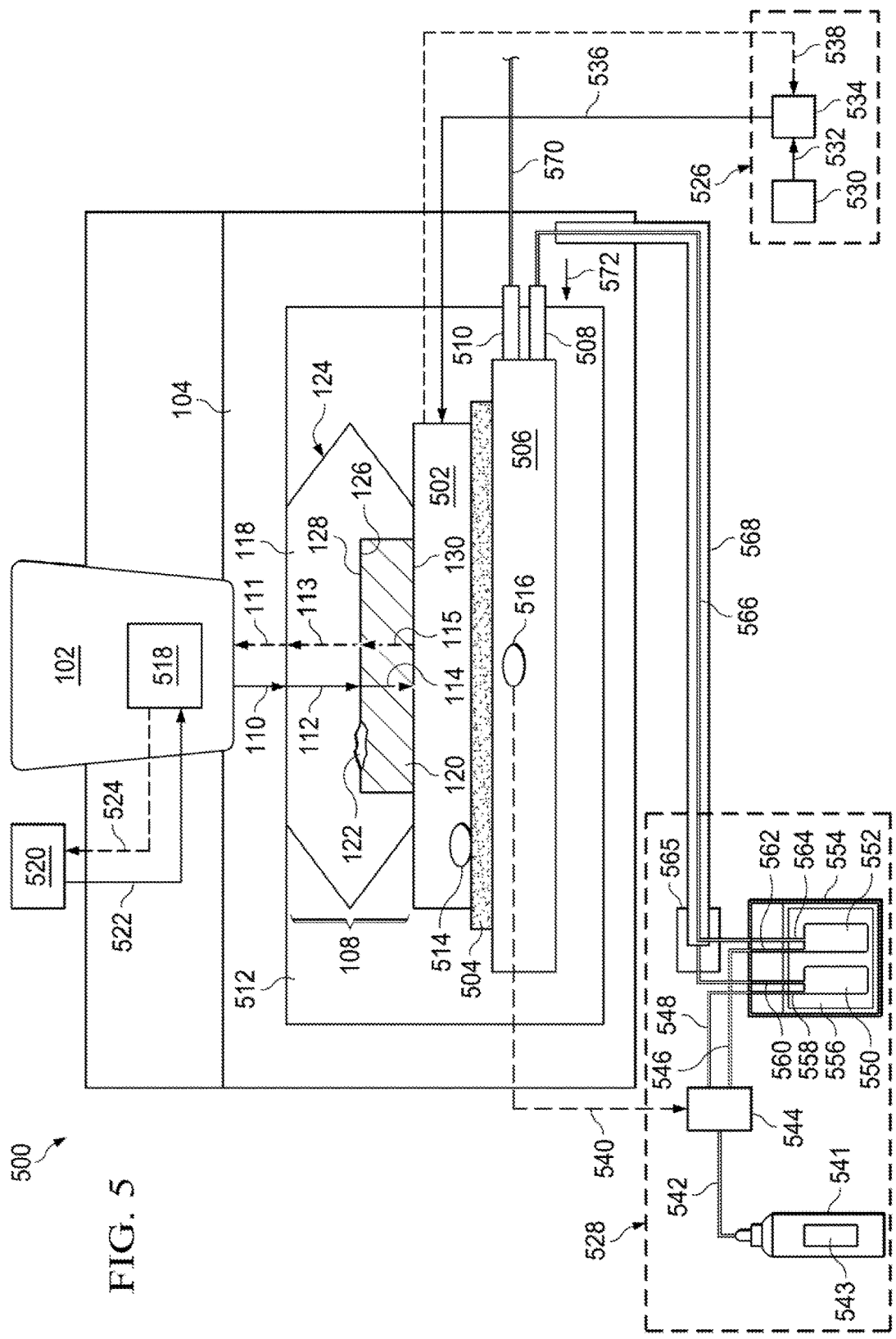
FIG. 5 illustrates a SAM system, in accordance with aspects of the present invention.

As shown in FIG. 5, SAM system 500 includes conventional SAM system 100 discussed above with reference to FIG. 1 without detector 106. In addition, SAM system 500 includes a heating/cooling device 502, a thermally conductive adhesive 504, a heat sink 506, a heat sink input device 508, a heat sink output device 510, insulation 512, a heat detecting device 514, a heat detecting device 516, a processing portion 518, a storage device 520, a transmit line 522, a receive line 524, a heating/cooling device control system 526 and a heat sink control system 528.

Heating/cooling device control system 526 includes a power supply 530, a control line 532, a temperature control unit 534, a temperature control line 536 and a temperature feedback line 538. Heat sink control system 528 includes a temperature feedback line 540, a nitrogen gas container 541, a nitrogen gas tube 542, a nitrogen gas supply 543, a temperature control unit 544, a nitrogen gas tube 546, a nitrogen gas tube 548, a heat exchanger copper tube coil 550, a heat exchanger copper tube coil 552, a dewar 554, a liquid nitrogen supply 556, a coil input 558, a coil output 560, a coil input 562, a coil output 564, an adapter 565, a nitrogen gas inner tube 566 and a nitrogen gas exterior tube 568.

DUT 108 is scanned using the same components and ultrasonic process described above with reference to FIG. 1 without detector 106 and without using transmissive ultrasonic wave 116. Components are added to conventional SAM system 100, in accordance with aspects of the present invention. Processing portion 518 is embedded in ultrasonic transducer 102. Storage device 520 is connected to processing portion 518 via transmit line 522 and receive line 524. Heating/cooling device 502 is placed beneath DUT 108. Thermally conductive adhesive 504 is placed beneath heating/cooling device 502. Heat sink 506 is placed beneath thermally conductive adhesive 504. Finally, insulation 512 surrounds DUT 108, heating/cooling device 502, thermally conductive adhesive 504 and heat sink 506. The subsystem surrounded with insulation 512 is submerged in acoustic conductive bath 104.

Heating/cooling device control system 526 monitors and controls the temperature of heating/cooling device 502. In this embodiment, heating/cooling device 502 is a Peltier device. However, any heating/cooling devices may used, non-limiting examples of which include coils. The temperature of heating/cooling device 502 is monitored by heat detecting device 514 via temperature feedback line 538. The temperature of heating/cooling device 502 is controlled by temperature control unit 534 via temperature control line 536. Temperature control unit 534 is powered by power supply 530 via control line 532.

Heat sink control system 528 monitors and controls the temperature of heat sink 506. The temperature of heat sink 506 is monitored by heat detecting device 516 via temperature feedback line 540. The temperature of heat sink 506 is controlled by temperature control unit 544. In this embodiment, heat sink control system 528 is a cooling system. Temperature control unit 544 receives a cooling liquid. In this example embodiment, the cooling liquid is nitrogen gas 543 from nitrogen gas container 541 via nitrogen gas tube 542. However, any liquid may be used that is able to transfer heat. Temperature control unit 544 then transmits nitrogen gas 543 to heat exchanger copper tube coils 550 and 552 via nitrogen gas tubes 546 and 548, respectively. Heat exchanger copper tube coils 550 and 552 receive nitrogen gas 543 via coil inputs 558 and 562, respectively. Heat exchanger copper tube coils 550 and 552 are submerged in liquid nitrogen 556 within dewar 554. Heat exchanger copper tube coils 550 and 552 then transmit nitrogen gas 543 to adapter 565 via coil outputs 560 and 564. Adapter 565 then converts coil outputs 560 and 564 into nitrogen gas inner tube 566 and nitrogen gas exterior tube 568, respectively. Nitrogen gas 543 then fills both nitrogen gas inner tube 566 and nitrogen gas exterior tube 568. The gas inside nitrogen gas inner tube 566 enters heat sink input device 508 via nitrogen input 572. Nitrogen gas 543 then fills heat sink 506 via heat sink input device 508 thusly cooling heat sink 506. Nitrogen exhaust 570 exits heat sink 506 via heat sink output device 510.

Storage device 520 stores values associated with various materials. Processing portion 518 stores these material values in storage device 520 via receive line 524, which is transmitted from processing portion 518. Conversely, the material values are retrieved by processing portion 518 via transmit line 522. Transmit line 522 is transmitted from storage device 520.

In accordance with aspects of the present invention, ultrasonic waves can be used to determine the thicknesses of layers in a DUT. For example, with reference to FIG. 5, the thickness of encapsulating shell 118 is calculated by recording both the velocity and time of flight for ultrasonic waves 110, 112 and 113. Distances that the ultrasonic waves travel may be determined by:

$$d_i = v_i t_i \tag{1}$$

where d is distance, v is velocity, t is time of flight and i is the ultrasonic wave under examination. Velocity is defined as speed travelled in a given direction. Time of flight is defined as the time duration travelled by the ultrasonic wave under examination. Thickness of encapsulating shell 118, for example, is then given by:

$$T = \frac{(d_2 + d_3) - d_1}{2} \tag{2}$$

where T is thickness, $d_1$ is distance travelled by ultrasonic wave 110, $d_2$ is distance travelled by ultrasonic wave 112 and $d_3$ is distance travelled by ultrasonic wave 113.

Figure 6A:
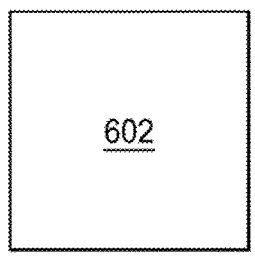
FIGS. 6A-C illustrate example planar views of various layers of a DUT as generated by a SAM system, in accordance with aspects of the present invention.
Figure 6B:
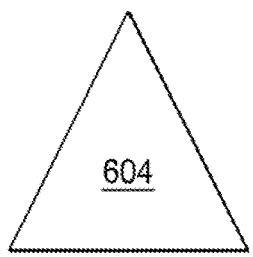
Figure 6C:
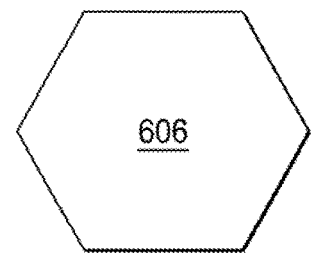

Returning to FIG. 3, after the thickness of each layer has been determined (S306) a normal scan is then performed on a DUT (S308). Planar images of the various layers are produced. For example, FIGS. 6A-C show planar views of layers 602, 604 and 606. FIGS. 6A-C will now be described in more detail.

In accordance with aspects of the present invention, the DUT would be rotated ninety degrees from the cross-sectional view so that a normal scan can be conducted on the device.

FIGS. 6A, 6B and 6C illustrate planar views of layers 602, 604 and 606, respectively, of a DUT from a SAM system, in accordance with aspects of the present invention.

Normal scans on the DUT determine the two-dimensional contour maps of each layer in a DUT. Planar views 602, 604 and 606 are examples of two-dimensional contour maps of three separate layers in the DUT.

Returning to FIG. 3, the materials of each layer of the DUT are then determined (S310). Processing portion 518 determines material values of each layer. The calculations associated with this function will now be described in further detail.

The material values for each layer of the DUT are given by:

$$\frac{E}{\rho} \tag{3}$$

where E is bulk modulus elasticity and ρ is specific density. The ratio, $$\frac{E}{\rho},$$

is a function of v. This function is expressed as:

$$v^2 = \frac{E}{\rho} \tag{4}$$

Velocity, v, is known from S306 above and is entered into equation (4) to determine the ratio, $$\frac{E}{\rho},$$

for each layer.

Processing portion 518 then measures and records the ratio, $$\frac{E}{\rho},$$

for each layer of the DUT. For example, typical materials found in integrated circuit packaging are silicon, mold compounds, epoxy, polyimide, copper, gold, alloy 42, lead and tin. Each of these materials has unique E and ρ values. Therefore, the ratio, $$\frac{E}{\rho},$$

for each material is also unique.

The ratio, $$\frac{E}{\rho},$$

for each material is then compared with many ratios of known materials that are stored in a database within storage device 520. Processing portion 518 then compares the ratio under examination with the stored ratios. If the ratio under examination does not match a stored ratio, then the ratio under examination is stored in the database. If the ratio under examination matches a stored ratio, then the material of the layer under examination is determined to be the material which correlates to the matched ratio.

Returning to FIG. 3, after the materials of each layer are determined (S310) a new area of the DUT is then moved to (S312). This starts to produce a two-dimensional contour map of the layer under examination. For example, as shown in FIGS. 6A-C, two-dimensional contour maps of layers 602, 604 and 606 are produced.

Returning to FIG. 3, another scan is then performed to determine the material of the new area (S314) as described above in S310.

It is then determined whether the entire area of the DUT has been scanned (S316).

If it is determined that the entire area has not been scanned (NO at S316), a new area is then moved to (S312).

Alternatively, if it is determined that the entire area has been scanned (YES at S316), then a two-dimensional contour map of the layer under examination is finished and method 300 then stops (S318).

A scan of a DUT, in accordance with aspects of the present invention, can be used to determine both thicknesses of layers and locations of delaminations. This will now be described in more detail in FIG. 7.

Figure 7:
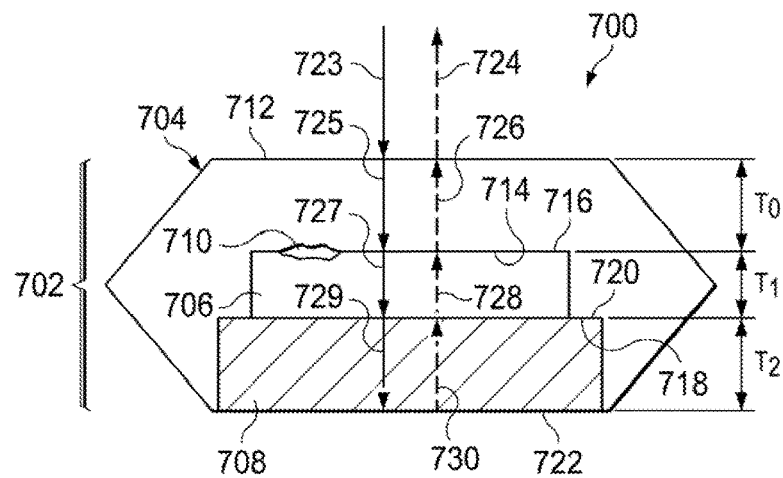
FIG. 7 illustrates a cross-sectional view of a DUT from a SAM system, in accordance with aspects of the present invention.

FIG. 7 illustrates a cross-sectional view 700 of a DUT 702 as scanned by a SAM system, in accordance with aspects of the present invention.

As shown in the figure, the cross-sectional view includes DUT 702. DUT 702 includes an encapsulating shell 704, an inner top layer 706, an inner bottom layer 708 and a delamination 710. Encapsulating shell 704 has a top surface 712, a bottom surface 714 and a thickness $T_0$. Inner top layer 706 has a top surface 716, a bottom surface 718 and a thickness $T_1$. Inner bottom layer 708 has a top surface 720, a bottom surface 722 and a thickness $T_2$.

Thicknesses $T_0$, $T_1$ and $T_2$ are determined in accordance with aspects of the present invention. The process for determining the thickness of a given layer is described above in S306, with reference to FIG. 3. For example, ultrasonic waves 723, 725 and 727 are used to determine thickness $T_0$ of encapsulating shell 704.

A scan, in accordance with aspects of the present invention, also locates imperfections/delaminations between layers. For example, delamination 710 is found by performing scans on both encapsulating shell 704 and inner top layer 706 to determine the separation between bottom surface 714 and top surface 716.

In addition to determining thicknesses of layers, material of layers, two-dimensional contour maps of layers and imperfections/delaminations between layers, the scanning method of the present invention as described in FIGS. 4-7 enables areas of delamination between layers to be accentuated using thermal stress testing. This will now be described in more detail in FIGS. 8A-E.

FIGS. 8A-E illustrate sample planar views 802, 808, 810, 816 and 822 of different layers of a DUT as generated by a SAM system.

Figure 8A:
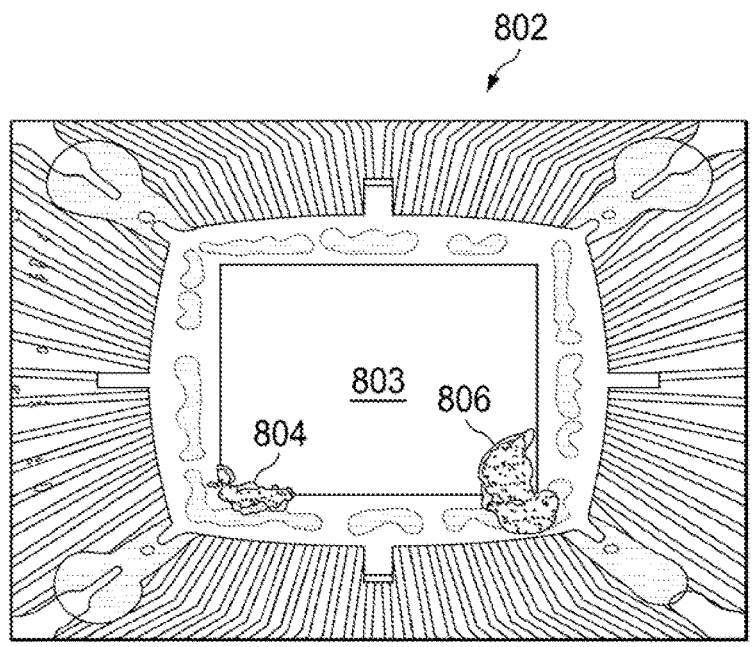
FIGS. 8A-E illustrate sample planar views of various layers of a DUT as generated by a SAM system.

As shown in FIG. 8A, planar view 802 includes a circuit 803, a delamination 804 and a delamination 806. Delaminations 804 and 806 depict areas of separation between adjacent layers within circuit 803. Delaminations 804 and 806 are accentuated by thermal stress testing, in accordance with aspects of the present invention. Circuit 803 is categorized as a defective device due to the detection of delaminations 804 and 806.

Figure 8B:
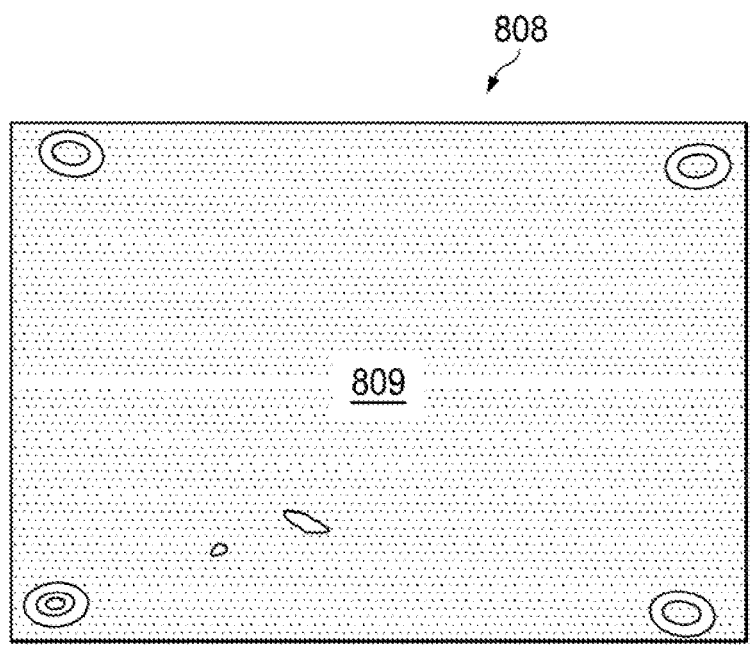

As shown in FIG. 8B, planar view 808 includes a circuit 809. Although circuit 809 underwent thermal stress testing, no delaminations were detected and circuit 809 is not categorized as a defective device.

Figure 8C:
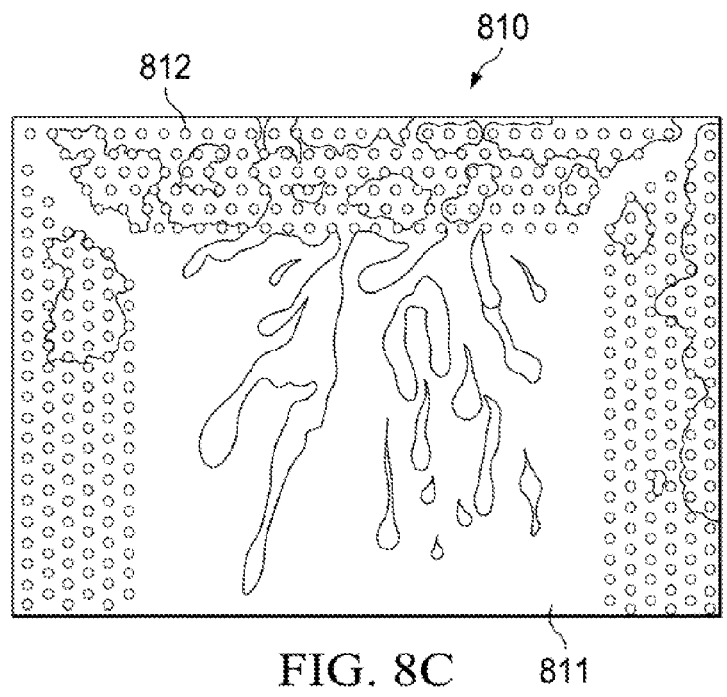

As shown in FIG. 8C, planar view 810 includes a circuit 811 and a delamination 812. Delamination 812 depicts an area of separation between adjacent layers of circuit 811. Delamination 812 is accentuated by thermal stress testing, in accordance with aspects of the present invention. Circuit 811 is categorized as a defective device due to the detection of delamination 812.

Figure 8D:
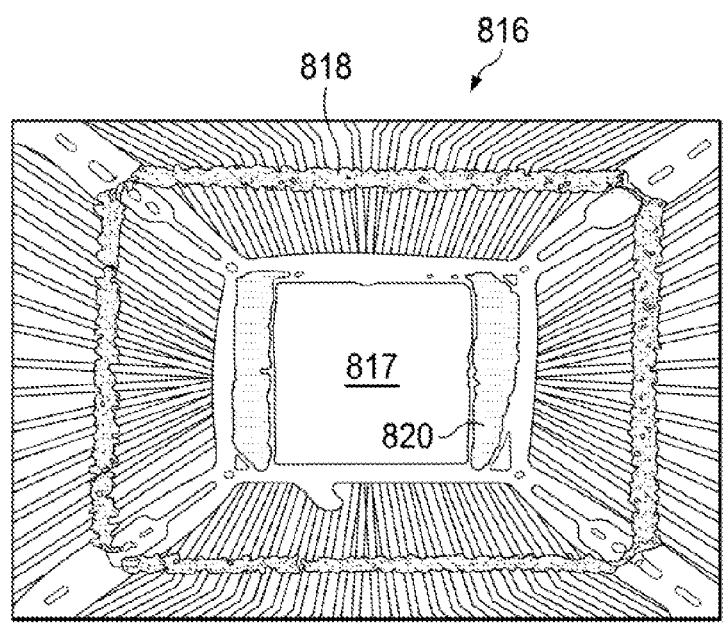

As shown in FIG. 8D, planar view 816 includes a circuit 817, a delamination 818 and a delamination 820. Delaminations 818 and 820 depict areas of separation between adjacent layers within circuit 817. Delaminations 818 and 820 are accentuated by thermal stress testing, in accordance with aspects of the present invention. Circuit 817 is categorized as a defective device due to the detection of delaminations 818 and 820.

Figure 8E:
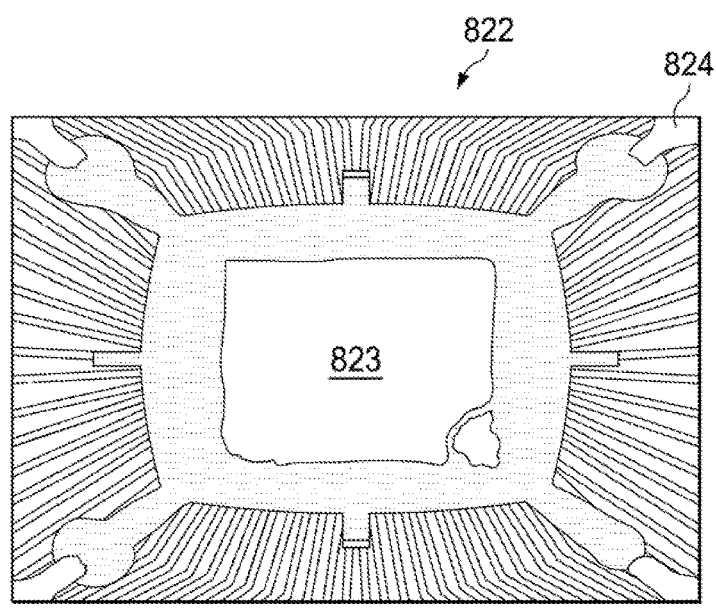

As shown in FIG. 8E, planar view 822 includes a circuit 823 and a delamination 824. Delamination 824 depicts an area of separation between adjacent layers within circuit 823. Delamination 824 is accentuated by thermal stress testing, in accordance with aspects of the present invention. Circuit 823 is categorized as a defective device due to the detection of delamination 824.

Thermal stress testing causes the materials of the various layers of a DUT to shrink or expand at various rates. The different rates of expansion/contraction increase the likelihood of developing a delamination between layers, thus exposing a faulty device. This will now be described in more detail in FIG. 9.

Figure 9:
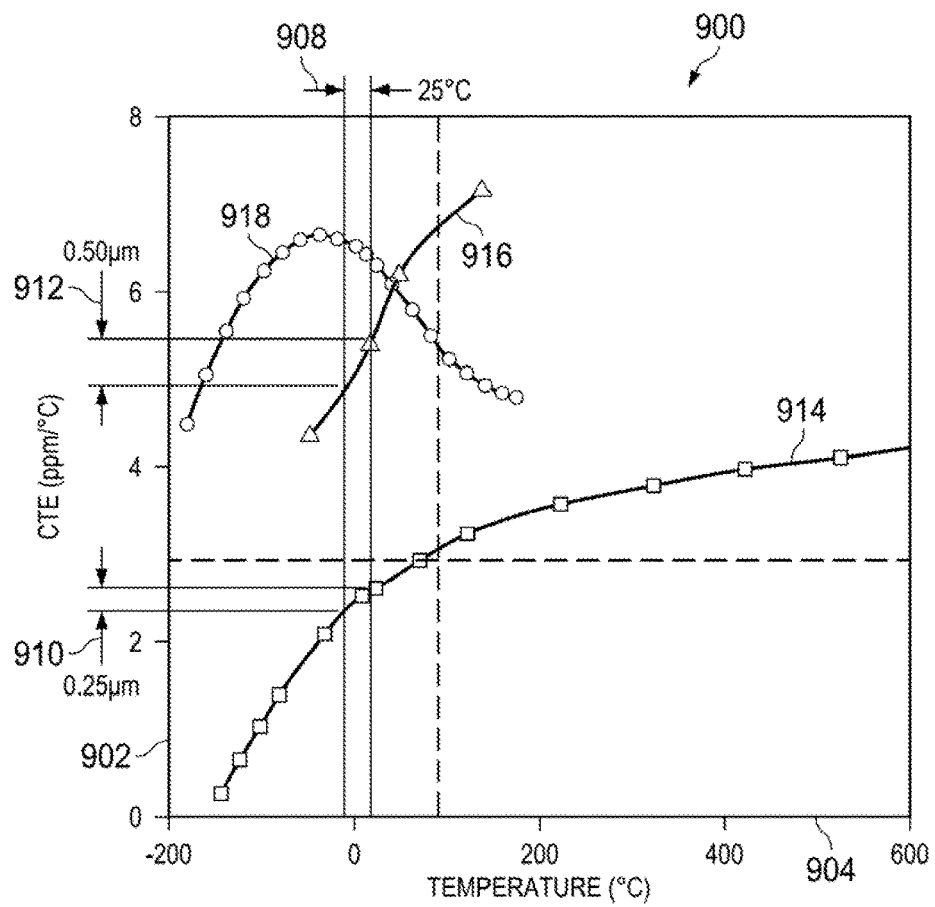
FIG. 9 illustrates a graph of temperature versus coefficient of thermal expansion of materials under an example thermal stress test.

FIG. 9 illustrates a graph 900 of temperature versus coefficient of thermal expansion of materials under an example thermal stress test.

As shown in the figure, graph 900 includes a y-axis 902, an x-axis 904, a function 914, a function 916 and a function 918.

Functions 914 and 916 show temperature versus coefficient of thermal expansion for the silicon and alumina, respectively. For purposes of discussion, let adjacent layers within a DUT be comprised of silicon and alumina, respectively. Further, for purposes of discussion, let the DUT be subjected to a 25° C. cooling. Silicon and alumina have different coefficients of thermal expansion. As such, while being subjected to a 25° C. cooling, the layer of silicon in the DUT will shrink at a different rate than the layer of alumina in the DUT.

As shown by the double lines 910 in the figure, the layer of silicon had shrunk by 0.25 micrometers. On the other hand, as shown by the double lines 912 in the figure, the layer of alumina had shrunk by 0.50 micrometers. The shrinkage difference between these two layers results in a gap of 0.25 micrometers. This gap is an example of delamination between adjacent layers.

It should be noted that a similar result may occur when a DUT is heated. In particular, the difference in expansion between two layers as a result of the difference in coefficients of thermal expansion may result in a delamination between adjacent layers.

An example thermal stress test includes heating, scanning and analyzing the DUT. This will now be described in more detail in FIG. 10.

Figure 10:
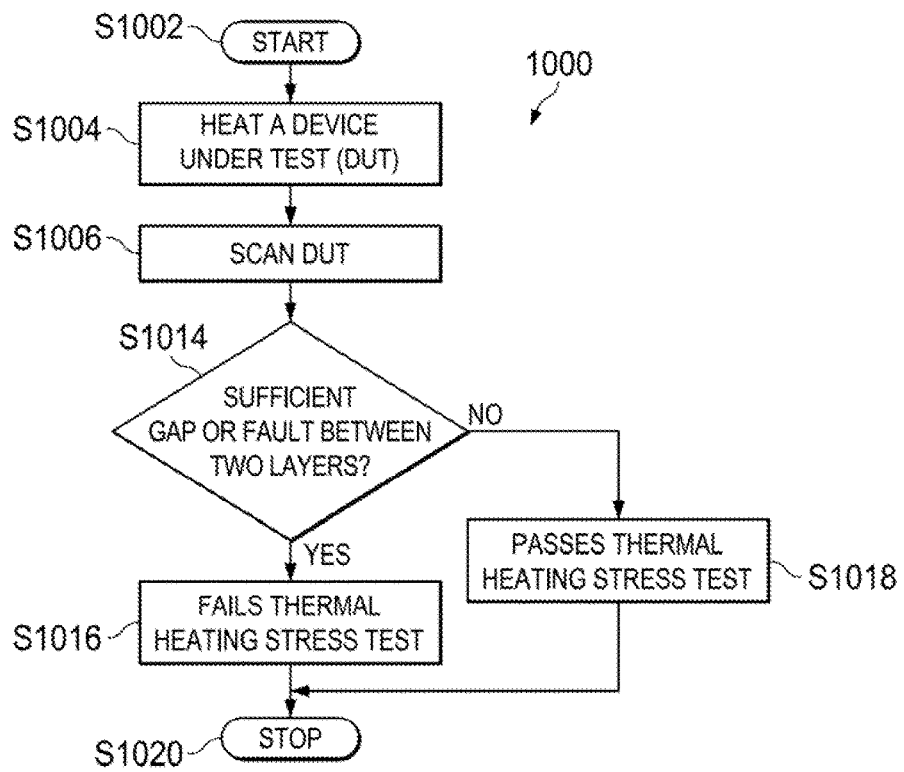
FIG. 10 illustrates an example method of a thermal heating stress test, in accordance with aspects of the present invention.

FIG. 10 illustrates an example method 1000 of a thermal heating stress test, in accordance with aspects of the present invention.

Method 1000 starts (S1002) and then a DUT is heated (S1004). With reference to FIG. 5, SAM system 500 may be used to heat DUT 108, in accordance with aspects of the present invention. This will now be described in further detail.

Temperature control unit 534 establishes a temperature threshold to which heating/cooling device 502 should be heated. This temperature threshold may be fixed within SAM system 500 or may be adjusted by way of a user input (not shown). For example, a user may be able to establish different temperature thresholds for different DUTs to be tested.

Once the temperature threshold is established, control unit 534 heats heating/cooling device 502 by way of temperature control line 536. In this example embodiment, heating/cooling device 502 is a Peltier device, such that power provided by temperature control unit 534 causes the side of the Peltier device that is adjacent to DUT 108 to heat up by increasing the temperature of DUT 108. Heat detecting device 514 monitors the temperature of the Peltier device and provides feedback to temperature control unit 534 by way of temperature feedback line 538. If the detected temperature by way of temperature feedback line 538 is not at the temperature threshold, then control unit 534 increases power to the Peltier device to continue to increase the temperature. If the detected temperature is above the temperature threshold, then control unit 534 decreases power to the Peltier device to decrease the temperature. This maintains a precise temperature of heating/cooling device 502. Further, a user may adjust the temperature threshold of heating/cooling device 502 by way of a user input (not shown).

To maintain accurate readings of the ultrasonic waves through acoustic conductive bath 104, a consistent temperature of the liquid within acoustic conductive bath 104 should be maintained. Insulation 512 prevents the liquid within acoustic conductive bath 104 from heating in the face of heating heating/cooling device 502 and heating DUT 108.

Even with insulation 512, the liquid within acoustic conductive bath 104 may heat up unless the heat generated by heating/cooling device 502 is removed. This is accomplished by transferring the heat from heat sink 506 with the use of fluid provided by heat sink control system 528.

In this embodiment, heating/cooling device 502 is a Peltier device and is used to heat DUT 108. As such, when power is provided to the Peltier device, the surface of the Peltier device adjacent to DUT 108 is heated from heat that is "pumped" from the opposite surface of the Peltier device, i.e., the surface adjacent to heat sink 506. As such, the surface of the Peltier device that is adjacent to heat sink 506 is cooled. Heat sink 506 is then used to provide heat to the cool side (bottom) of the Peltier device, so that heat can be pumped to DUT 108 in order to maintain a constant temperature. This is accomplished by providing hot fluid to heat sink 506 by way of heat sink control system 528. The difference between this embodiment and the embodiment discussed above with reference to FIG. 5 is that the former uses a cold fluid (nitrogen) whereas the latter uses a high temperature fluid that is able to provide heat for heat transfer. Any known fluid may be used that is able to provide heat for heat transfer.

Returning to FIG. 10, after a DUT is heated (S1004), a scan is then performed on the DUT (S1006). For example, with reference to FIG. 5, SAM system 500 may be used to scan DUT 108, in accordance with aspects of the present invention.

Returning to FIG. 10, it is then determined whether there exists a sufficient gap between adjacent layers (S1014). For example, with reference to FIG. 8A, delaminations 804 and 806 indicate that there exist sufficient gaps between adjacent layers within circuit 803. Alternatively, with reference to FIG. 8B, planar view 808 indicates that there exist no sufficient gaps/delaminations between adjacent layers within circuit 809. The establishment of gap thresholds will now be described in more detail with reference to FIG. 5.

Processing portion 518 establishes a gap threshold between layers to which delaminations should be determined. This gap threshold may be fixed within SAM system 500 or may be adjusted by way of a user input (not shown). For example, a user may be able to establish different gap thresholds for different DUTs to be tested.

This gap threshold is used as a baseline to classify a DUT as being satisfactory or deficient. In particular, if the DUT is determined to have a delamination that is equal to or greater than the predetermined gap threshold, then the DUT is deficient. On the other hand, if the DUT is determined to have no delaminations that are equal to or greater than the predetermined gap threshold, then the DUT is satisfactory. With reference to FIG. 5, processing portion 518 compares the area of separation between encapsulating shell 118 and inner layer 120 with the predetermined gap threshold. If the area of delamination 122 is equal to or greater than the predetermined gap threshold, then DUT 108 fails the thermal stress test and is subsequently categorized as a faulty device. It should be noted that in this example, the predetermined gap threshold is an area. However, the predetermined gap threshold may be distance in one direction, distance in a plurality of directions, distance normal to heating/cooling device 502, and combinations thereof.

For purposes of discussion, with reference to FIG. 8A, suppose delaminations 804 and 806 were determined to be equal to or greater than a predetermined gap threshold. In this example, circuit 803 would then be categorized as a faulty device, having failed the thermal stress test. Alternatively, with reference to FIG. 8B, in circuit 809, there were no areas of separation between layers determined to be equal to or greater than the predetermined gap threshold. Therefore, circuit 809 would then be categorized as a sufficient device, having passed the thermal stress test.

Returning to FIG. 10, if it is determined that there exists a sufficient gap between adjacent layers (YES at S1014), the DUT then fails the thermal stress test (S1016). Method 1000 then stops (S1020).

Alternatively, if it is determined that there exists no sufficient gap between adjacent layers (NO at S1014), the DUT then passes the thermal stress test (S1018). Method 1000 then stops (S1020). Another example thermal stress test includes cooling, scanning and analyzing the DUT. This will now be described in more detail in FIG. 1I.

Figure 11:
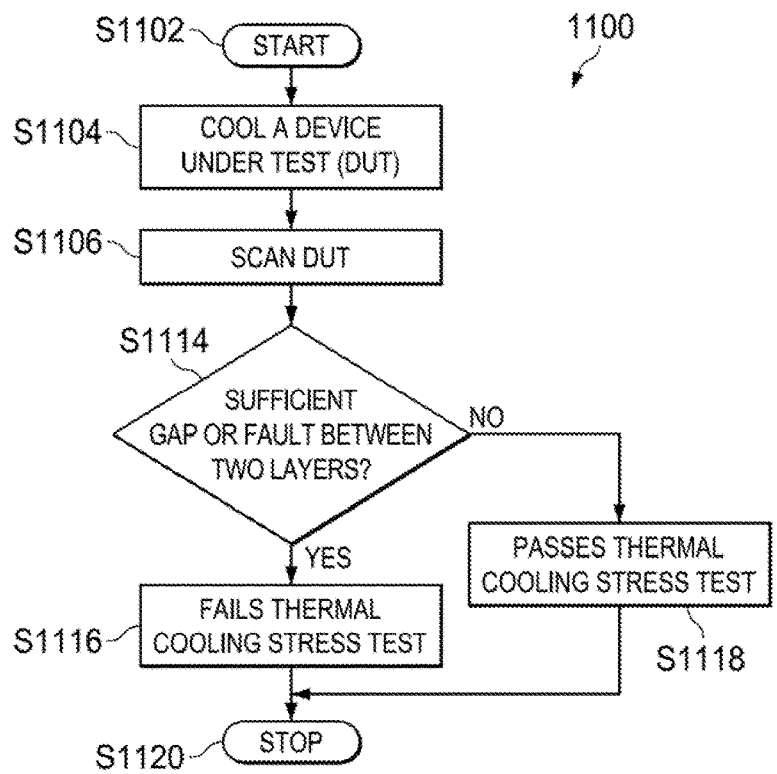
FIG. 11 illustrates an example method of a thermal cooling stress test, in accordance with aspects of the present invention.

FIG. 11 illustrates an example method 1100 of a thermal cooling stress test, in accordance with aspects of the present invention.

Method 1100 starts (S1102) and then a DUT is cooled (S1104). For example, with reference to FIG. 5, SAM system 500 may be used to cool DUT 108, in accordance with aspects of the present invention. This will now be described in further detail.

Temperature control unit 534 establishes a temperature threshold to which heating/cooling device 502 should be cooled. This temperature threshold may be fixed within SAM system 500 or may be adjusted by way of a user input (not shown). For example, a user may be able to establish different temperature thresholds for different DUTs, to be tested.

Once the temperature threshold is established, control unit 534 cools heating/cooling device 502 by way of temperature control line 536. In this example embodiment, heating/cooling device 502 is a Peltier device, such that power provided by temperature control unit 534 causes the side of the Peltier device that is adjacent to DUT 108 to cool down, thus decreasing the temperature of DUT 108. Heat detecting device 514 monitors the temperature of the Peltier device and provides feedback to temperature control unit 534 by way of temperature feedback line 538. If the detected temperature by way of temperature feedback line 538 is not at the temperature threshold, then control unit 534 increases power to the Peltier device to continue to decrease the temperature. If the detected temperature is below the temperature threshold, then control unit 534 decreases power to the Peltier device to increase the temperature. This maintains a precise temperature of heating/cooling device 502. Further, a user may adjust the temperature threshold of heating/cooling device 502 by way of a user input (not shown).

To maintain accurate readings of the ultrasonic waves through acoustic conductive bath 104, a consistent temperature of the liquid within acoustic conductive bath 104 should be maintained. Insulation 512 prevents the liquid within acoustic conductive bath 104 from cooling in the face of cooling heating/cooling device 502 and cooling DUT 108.

Even with insulation 512, the liquid within acoustic conductive bath 104 may cool down unless the heat generated by heating/cooling device 502 is removed. This is accomplished by transferring the cold from heat sink 506 with the use of fluid provided by heat sink control system 528.

In this embodiment, since the Peltier device is used to cool DUT 108, the top of the Peltier device is cooled whereas the bottom of the Peltier device is heated. Heat sink 506 is then used to provide cooling to the hot side (bottom) of the Peltier device in order to maintain a constant temperature. This is accomplished by providing cold fluid to heat sink 506 by way of heat sink control system 528.

Returning to FIG. 11, after a DUT is cooled (S1104), a scan is then performed on the DUT (S1106). For example, with reference to FIG. 5, SAM system 500 may be used to scan DUT 108, in accordance with aspects of the present invention.

Returning to FIG. 11, it is then determined whether there exists a sufficient gap between adjacent layers (S1114). For example, with reference to FIG. 8A, delaminations 804 and 806 indicate that there exist sufficient gaps between adjacent layers within circuit 803. Alternatively, with reference to FIG. 8B, planar view 808 indicates that there exist no sufficient gaps/delaminations between adjacent layers within circuit 809. Both the establishment of gap thresholds and examples of using the gap thresholds to locate areas of delamination are described above in S1014.

Returning to FIG. 11, if it is determined that there exists a sufficient gap between adjacent layers (YES at S1114), the DUT then fails the thermal stress test (S1116). Method 1100 then stops (S1120).

Alternatively, if it is determined that there exists no sufficient gap between adjacent layers (NO at S1114), the DUT then passes the thermal stress test (S1118). Method 1100 then stops (S1120). Conventional SAM systems sometimes provide inadequate processes for determining areas of delamination between adjacent layers in a DUT. Although they may detect areas of delamination in some cases, in other cases, conventional SAM systems may not detect areas of delamination. In the latter cases, areas of delamination are found only after the defective DUTs are in use.

One aspect of the present invention provides a SAM system and method for determining areas of delamination between adjacent layers. By heating/cooling a DUT, areas of delamination between adjacent layers are accentuated and can easily be spotted in images of the DUT. Such images are produced via ultrasonic scans. If adjacent layers expand/contract sufficiently enough to create a gap, then the DUT may be discarded. This may allow an entire batch of DUTs to be categorized as faulty and subsequently discarded prior to their use.

Another aspect of the present invention provides a system and method for monitoring and precisely controlling the temperature of the SAM system. This control system provides a way to experiment with various temperatures for a DUT to ensure that areas of delamination are found. This is important because the present invention is capable of being used for a multitude of DUTs that are comprised of a multitude of materials. The temperature that is used to find areas of delamination in one DUT may not be equal to the temperature that is used to find areas of delamination in a different DUT.

Another aspect of the present invention provides a system and method for determining other substantive properties of a DUT, such as two-dimensional topological maps of the various layers. This allows the surfaces and conditions of the various layers of the DUT to be known and analyzed.

The foregoing description of various preferred embodiments of the invention have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed as new and desired to be protected by Letters Patent of the United States is:

1. A method comprising:
   submerging a device under test in an acoustic conductive bath, the device under test having a top layer and a second layer, the top layer being disposed between the second layer and the conductive bath, the top layer having a top surface in contact with the conductive bath;
   scanning, via an ultrasonic transducer, an area of the device under test;
   obtaining, via a processor, a contour map of the top layer from said scanning;
   determining, via the processor, a velocity of an acoustic wave through the top layer from said scanning;
   storing, in a storage device, values corresponding to a plurality of materials, respectively, each value being a function of the bulk modulus elasticity of a respective material and a function of the specific density of the respective material;
   determining, via the processor, a top layer value based on the determined velocity;
   comparing, via the processor, the top layer value with the stored values; and
   determining which of the plurality of materials the top layer comprises based on said comparing.

2. The method of claim 1, further comprising determining, via the processing portion, a thickness of the top layer from said scanning.

3. The method of claim 1, further comprising:
   heating, via a heating component, the device under test to a predetermined temperature such that the top layer expands a first amount and such that the second layer expands a second amount;
   scanning, via the ultrasonic transducer, a second area of the device under test; and
   determining whether a gap forms, between the first layer and the second layer, greater than a predetermined threshold.

4. The method of claim 3,
   wherein said submerging comprises disposing the device under test on a Peltier device, which is disposed on a heat sink, and
   wherein said heating comprises providing power to the Peltier device so as to heat the device under test.

5. The method of claim 4, further comprising:
   detecting the temperature of one of the device under test and the Peltier device; and
   modifying the power provided to the Peltier device when one of the detected temperature is lower than a first predetermined temperature threshold and the detected temperature is greater than a second predetermined temperature threshold.

6. The method of claim 4, further comprising:
   detecting the temperature of one of the device under test and the Peltier device; and
   modifying a temperature of the heat sink when one of the detected temperature is lower than a first predetermined temperature threshold and the detected temperature is greater than a second predetermined temperature threshold.

7. The method of claim 6, wherein said modifying a temperature of the heat sink comprises circulating liquid through the heat sink.

8. The method of claim 1, further comprising:
   determining, via the processor, a velocity of an acoustic wave through the second layer from said scanning;
   determining, via the processor, a second layer value based on the determined velocity;
   comparing, via the processor, the second layer value with the stored values; and
   determining which of the plurality of materials the second layer comprises based on said comparing.

9. The method of claim 8, further comprising determining, via the processor, a thickness of the second layer from said scanning.

10. The method of claim 8, further comprising:
    determining, via the processor, a velocity of an acoustic wave through a third layer from said scanning;
    determining, via the processor, a third layer value based on the determined velocity;
    comparing, via the processor, the third layer value with the stored values; and
    determining which of the plurality of materials the third layer comprises based on said comparing.

11. The method of claim 10, further comprising determining, via the processor, a thickness of the third layer from said scanning.

12. The method of claim 10, further determining whether there are areas of delamination between the second layer and the third layer.

13. The method of claim 1, further determining whether there are areas of delamination between the top layer and the second layer.

14. A method, comprising:
    submerging a device in an acoustic conductive bath, the device having a top layer and a second layer, the top layer disposed between the second layer and the conductive bath, the top layer having a top surface in contact with the conduct bath;
    heating the device under test to a predetermined temperature such that the top layer expands a first amount and such that the second layer expands a second amount;
    scanning, via an ultrasonic transducer, an area of the device under test; and
    determining whether a gap forms between the top and second layers of the device.

15. The method of claim 14,
    wherein the submerging comprises disposing the device under test on a Peltier device, which is disposed on a heat sink, and
    wherein said heating comprises providing power to the Peltier device so as to heat the device under test.

16. The method of claim 14, wherein the heating is implemented via a heating element.

17. The method of claim 16, wherein the heating element is adjacent the device.

18. The method of claim 16, wherein the heating element contacts the device.

19. The method of claim 14, further including determining if there are areas of delamination.

20. The method of claim 14, further comprising:
    determining, via the processor, a velocity of an acoustic wave through the second layer from said scanning;
    determining, via the processor, a second layer value based on the determined velocity;
    comparing, via the processor, the second layer value with the stored values; and
    determining which of the plurality of materials the second layer comprises based on said comparing.

21. The method of claim 20, further comprising determining, via the processor, a thickness of the second layer from said scanning.

22. The method of claim 21, further comprising:
determining, via the processor, a velocity of an acoustic wave through a third layer from said scanning;
determining, via the processor, a third layer value based on the determined velocity;
comparing, via the processor, the third layer value with the stored values; and
determining which of the plurality of materials the third layer comprises based on said comparing.

23. The method of claim 21, further comprising determining, via the processor, a thickness of the third layer from said scanning.

24. The method of claim 21, further determining whether there are areas of delamination between the top layer and the second layer.

25. The method of claim 21, further determining whether there are areas of delamination between the second layer and the third layer.

26. A method, comprising:
submerging a semiconductor device in an acoustic conductive bath;
heating the semiconductor device to a predetermined temperature;
scanning, via an ultrasonic transducer, an area of the semiconductor device under test; and
determining whether a gap forms between layers of the semiconductor device.

27. The method of claim 26, wherein the semiconductor device has a top layer and a second layer, the top layer disposed between the second layer and the conductive bath, the top layer having a top surface in contact with the conduct bath.

28. A device tested for delamination between layers within the device, the testing comprising:
submerging a device under test in an acoustic conductive bath, the device under test having a top layer and a second layer, the top layer being disposed between the second layer and the conductive bath, the top layer having a top surface in contact with the conductive bath;
scanning, via an ultrasonic transducer, an area of the device under test;
obtaining, via a processor, a contour map of the top layer from said scanning;
determining, via the processor, a velocity of an acoustic wave through the top layer from said scanning;
storing, in a storage device, values corresponding to a plurality of materials, respectively, each value being a function of the bulk modulus elasticity of a respective material and a function of the specific density of the respective material;
determining, via the processor, a top layer value based on the determined velocity;
comparing, via the processor, the top layer value with the stored values; and
determining which of the plurality of materials the top layer comprises based on said comparing.

29. A device tested for delamination between layers within the device, the testing comprising:
submerging a device in an acoustic conductive bath, the device having a top layer and a second layer, the top layer disposed between the second layer and the conductive bath, the top layer having a top surface in contact with the conduct bath;
heating the device under test to a predetermined temperature such that the top layer expands a first amount and such that the second layer expands a second amount;
scanning, via an ultrasonic transducer, an area of the device under test; and
determining whether a gap forms between the top and second layers of the device.

30. A semiconductor device tested for delamination between layers within the semiconductor device, the testing comprising:
submerging a semiconductor device in an acoustic conductive bath;
heating the semiconductor device to a predetermined temperature;
scanning, via an ultrasonic transducer, an area of the semiconductor device under test; and
determining whether a gap forms between layers of the semiconductor device.

* * * * *